United States Patent [19]

McMahan

[11] Patent Number: 5,681,307

[45] Date of Patent: Oct. 28, 1997

[54] FIBER-OPTIC PLUG AND RECEPTACLE PROVIDING AUTOMATIC APPLIANCE RECOGNITION

[76] Inventor: William H. McMahan, P.O. Box 636. 14966 State Hwy. 410, Robertson, Wyo. 82944

[21] Appl. No.: 329,479

[22] Filed: Oct. 26, 1994

[51] Int. Cl.$^6$ ............................................. A61N 5/06
[52] U.S. Cl. ...................... 606/12; 606/10; 606/11; 606/15; 606/16
[58] Field of Search ............... 606/2, 3–18; 600/117, 600/118, 132

[56] References Cited

U.S. PATENT DOCUMENTS

| | | | |
|---|---|---|---|
| 4,503,854 | 3/1985 | Jako | 606/11 |
| 4,580,557 | 4/1986 | Hertzmann . | |
| 4,633,872 | 1/1987 | Chaffee et al. | 606/11 |
| 4,722,337 | 2/1988 | Looch et al. . | |
| 4,907,588 | 3/1990 | Burston | 606/11 |
| 5,157,750 | 10/1992 | Grace et al. | 606/10 |
| 5,400,267 | 3/1995 | Denen et al. | 600/118 |

FOREIGN PATENT DOCUMENTS

| | | | |
|---|---|---|---|
| 408160 | 1/1991 | European Pat. Off. | 606/2 |
| 2211 958 | 12/1989 | United Kingdom . | |

Primary Examiner—David M. Shay
Attorney, Agent, or Firm—Thorpe, North & Western, L.L.P.

[57] ABSTRACT

The present invention provides a system for communicating information from a detachable appliance to a base unit so that the base unit can calibrate its operation to match the characteristics of the detachable appliance. The invention has particular benefits when used with medical lasers. A receptacle, mounted on the laser base unit, is provided for operatively receiving a plug on the appliance and transferring energy from the base unit to the detachable appliance. To convey information about the appliance from the appliance to the base unit, an information bearing surface is mounted on the plug and is oriented substantially perpendicularly to the external surface of the plug. The information bearing surface includes a plurality of information zones which are each machine readable and optically readable by the base unit. The base unit includes components for optically detecting and decoding the information embedded in the information zones when the plug is received by the receptacle. The structure of the present invention included on the appliance is reliable and does not appreciably increase the cost of the appliance and thus can be disposed of after a single use. Moreover, appliances provided with the present invention can still be used with base units which are not equipped in accordance with the present invention to detect the information presented on the appliance.

4 Claims, 6 Drawing Sheets

FIBER-OPTIC PLUG AND RECEPTACLE PROVIDING AUTOMATIC APPLIANCE RECOGNITION

BACKGROUND

1. The Field of the Invention

This invention relates to laser devices wherein the laser energy is delivered via a fiber-optic appliance which is disconnectable from the laser device. More particularly, the present invention is related to medical laser devices wherein any one of a variety of fiber-optic appliances can be removably attached to the laser device.

2. The Prior Art

Lasers have become powerful tools in science, industry, and medicine. It is common to convey laser light via an optical fiber guide between a laser and the site where the laser light is to be delivered. For example, the laser device can be housed in a relatively large cabinet with the laser light conveyed to and exiting a hand held probe. The use of a light weight hand held probe at the end of a optical fiber guide allows a user to easily and accurately direct the laser beam. Various appliances, each directed to a particular task, can be connected to the laser.

In medical applications, it is particularly advantageous to dispose of the appliance after each use. Disposing of the appliance after each use ensures that patients will not be cross infected and that each appliance is properly working at the start of a procedure.

Particularly in the case of lasers and appliances used in medical procedures, the characteristics of the appliance and the output of the laser must be matched for proper operation. For example, each appliance has a maximum continuous wave power handling capacity, a range of wavelengths at which operation is most efficient, a laser pulse width which is most effective, limitations as to duty cycle, the total energy which can be delivered per pulse train, and so forth. If the characteristics of the appliance and the laser are mismatched, inefficient operation occurs at best and, at worst, patient injury will occur.

In order to provide economical laser treatment equipment, it is common to provide a laser device whose output can be calibrated to accommodate a number of different appliances. For example, one appliance may require high power pulse of a short duration while another appliance may require a low power pulse of a long duration. In many instances, the adjustment of the laser device to provide an output which is suitable for the appliance is manually accomplished by the operator. Leaving it to the operator to manually adjust or calibrate the laser parameters is, however, fraught with the possibility of error. Improper adjustment can, and has, caused serious patient harm. Thus, there have been numerous attempts in the art to automatically match or calibrate a laser's output characteristics to any one of a plurality of appliances.

Examples of apparatus which are intended to automatically match a medical laser's output to a variety of appliances are set forth in U.S. Pat. Nos. 4,580,557 and 4,722,337 and in United Kingdom Patent Publication No. 2 211 958. The apparatus described in these references provide that a medical laser can be automatically matched or calibrated for a particular appliance.

While the schemes described in the mentioned references provide automatic matching or calibration, they inherently have several critical drawbacks. Since the appliances in medical applications are disposed of after a single use, whatever apparatus is used to provide automatic matching or calibration cannot appreciably increase the cost of the appliance. Some of the schemes disclosed in the known art excessively increases the cost of the appliance.

It is also desirable that the approach used to provide automatic matching or calibration should convey to a laser device a large number of parameters thus allowing precise calibration to a wide variety of appliances. Due to the arrangement of the prior schemes, the amount of information which an appliance can convey to a laser is often severely limited. Moreover, the prior schemes disclosed in these references result in appliances which can only be used with laser devices already equipped with the proper structures. In view of the forgoing, it would be an advance in the art to provide an apparatus which overcomes these problems.

BRIEF SUMMARY AND OBJECTS OF THE INVENTION

In view of the above described state of the art, the present invention seeks to realize the following objects and advantages.

It is a primary object of the present invention to provide a connector which can simply and reliably convey information between the plug and the receptacle of a connector.

It is also an object of the present invention to provide a fiber-optic plug and receptacle which provides automatic recognition of an appliance which is convenient and reliable and which is particularly adapted for use with medical lasers.

It is a further object of the present invention to provide a fiber-optic plug and receptacle which provides automatic recognition of an appliance connected to a medical laser which is inexpensive.

It is a still further object of the present invention to provide a fiber-optic plug and receptacle which provides automatic recognition of an appliance connected to a medical laser wherein the information conveying feature of the plug is inexpensive enough to allow the appliance and plug to be disposed of after a single use.

It is also an object of the present invention to provide a fiber-optic connector which prevents improper calibration of a medical laser.

It is a further object of the present invention to provide a fiber-optic plug and receptacle which provides automatic recognition of the characteristics of the appliance connected to the plug wherein the plug is still compatible with receptacles which are not equipped to detect the information conveyed by the plug.

It is yet another object of the present invention to provide a fiber-optic plug and receptacle which prevents use of unsafe combinations of appliances and medical lasers.

These and other objects and advantages of the invention will become more fully apparent from the description and claims which follow, or may be learned by the practice of the invention.

The present invention provides a system for communicating information from a detachable appliance to a base unit so that the operation of the base unit comply with the characteristics of the detachable appliance. The present invention is particularly applicable for use with medical lasers which typically have a base unit, housing the laser device, to which are attached any one of a number of appliances, including single use (i.e., disposable) appliances, which each typically require that the laser be operated differently for proper usage. Improper operation of the laser device for the particular appliance at results in inefficient operation and can result in injury to a patient being treated using the laser device or to a medical practitioner.

One preferred example of the present invention provides that the operation of the base unit is automatically adjusted for the particular appliance which is inserted into the receptacle of the base unit. One preferred example of present invention includes a plug means for receiving energy which is output from the base unit. A means, such as an optical fiber, for conveying energy received from the base unit to a location away from the base unit, such as to a hand tool at the patient is also provided.

In the preferred examples of the invention a receptacle means, mounted on the base unit, is provided for operatively receiving the plug and transferring energy from the base unit to the detachable appliance. In the preferred embodiments, a means for aligning the optical fiber with the receptacle means is provided, precise alignment being critical in many applications.

To convey information about the appliance from the appliance to the base unit, an information bearing means, mounted on the plug means and preferably oriented substantially perpendicularly to the external surface of the plug means, is provided. The information bearing means includes a plurality of information zones which are machine readable and optically readable by the base unit. A coded symbol means provided on the information bearing means conveys information concerning proper and safe operation of the laser base unit and appliance combination. In one preferred embodiment, the coded symbol means comprises the plurality of information zones each selectively consisting of a substantially optically reflective material or a substantially optically nonreflective material having an annular ring shape.

It is preferred that the information zones be arranged so that each information zone is passed over by a line extending tangentially from the fiber which extends through the plug means. The number of information zones can be increased or decreased in accordance with the amount of information which needs to be conveyed. The information which is conveyed can include operating instructions to the base unit, appliance identification information, and messages to be delivered to the operator of the laser device.

The base unit includes means for detecting the presence of a reflecting or nonreflecting material in each of the information zones when the plug is received by the receptacle means. The base unit also includes means for decoding the information conveyed by the coded symbol means such that one or more appliances or characteristics of the appliances can be identified by the base unit.

The structure of the present invention included on the appliance is reliable and does not appreciably increase the cost of the appliance and thus the appliance can be disposed of after a single use if desired. Moreover, appliances provided with the present invention can still be used with base units which are not equipped with the present invention to detect the information presented on the appliance.

BRIEF DESCRIPTION OF THE DRAWINGS

In order to better appreciate how the above-recited and other advantages and objects of the invention are obtained, a more particular description of the invention briefly described above will be rendered by reference to specific embodiments thereof which is illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Reference will now be made to the drawings wherein like structures will be provided with like reference designations.

Figure 1:
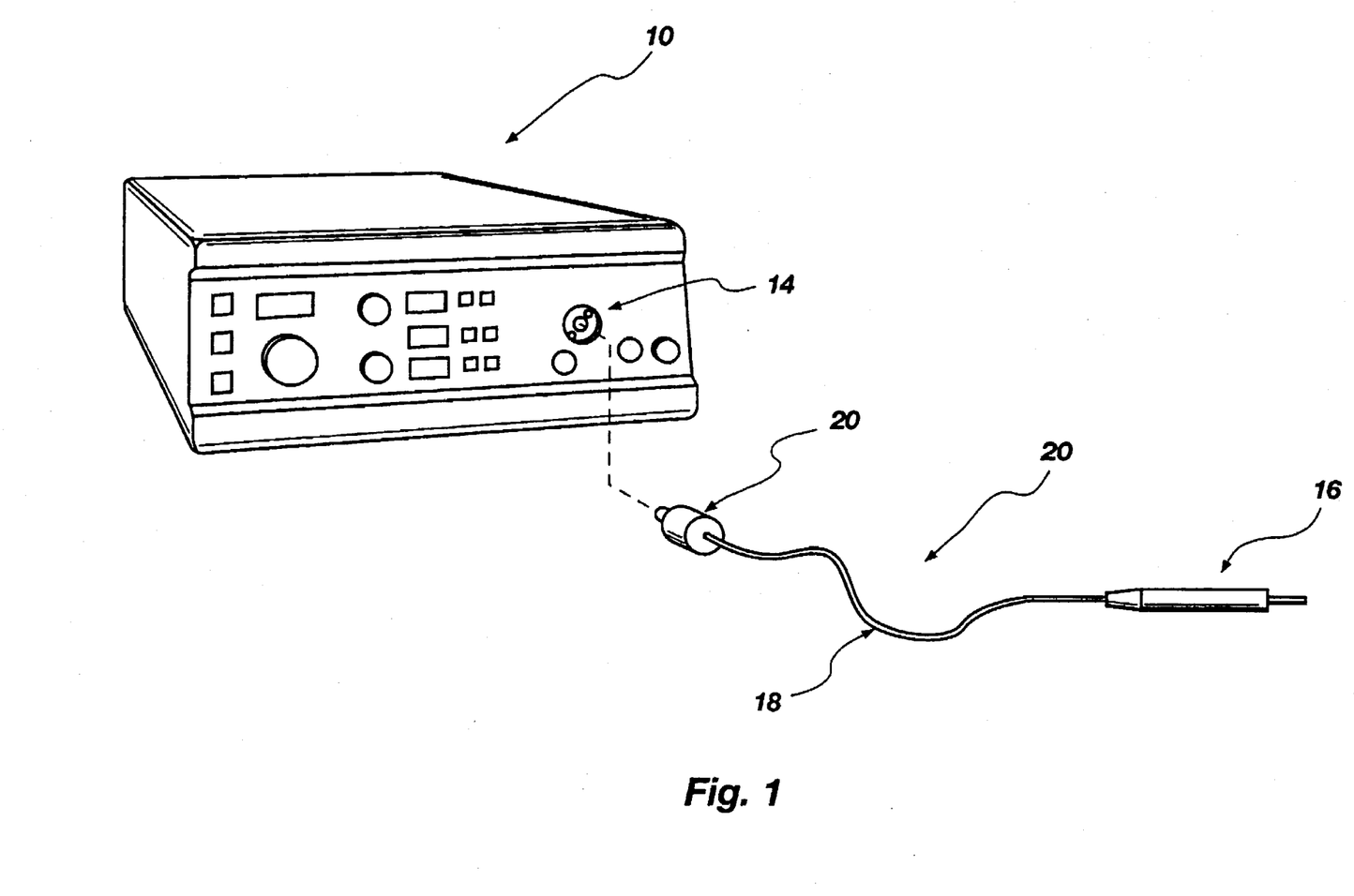
FIG. 1 is a representation of a laser device and an accompanying fiber-optic appliance.

FIG. 1 shows a laser device, configured as a base unit and generally designated at 10, and a fiber-optic appliance, generally designated at 12. The laser device 10 can be adapted from any one of a number of laser devices available in the art but it is particularly preferred to be a medical laser device.

As explained earlier, the use of medical lasers generally requires the setting or calibration of the medical laser's various operating parameters. The setting or calibration of the laser device 10 matches the laser output to the specific application of the instrument or device, e.g., appliance 12, with which it is to be operated. Laser parameters such as wavelength, laser intensity, total energy delivered, and so forth must be matched to the varying optical properties, i.e., wavelength and power limitations, of the different appliances which are attached to the laser device 10. Additional parameters which are important to the operation of a medical laser will be described in further detail later in this disclosure.

In the case of a medical laser used to treat a patient, miscalibration can result in serious harm. Thus, automatic calibration of the laser device 10 for the requirements of the appliance 12, which is simple and inexpensive to carry out, is very desirable but has not been provided in the art.

Still referring to FIG. 1, the appliance can preferably comprise a hand piece, generally indicated at 16, and a fiber-optic connector plug, generally indicated at 20, the hand piece 16 and the fiber-optic connector plug 20 being connected by an optical fiber assembly, generally indicated at 18. The laser device 10 is provided with a receptacle, generally designated at 14, into which the plug 20 is received to communicate laser light which is output from the laser device 10.

While the embodiments of the present invention are described herein in a medical laser application, it will be appreciated that the present invention has application in any application where it would be advantageous to have a plug convey information to a device having a receptacle which receives the plug.

Figures 2, 3, 4:
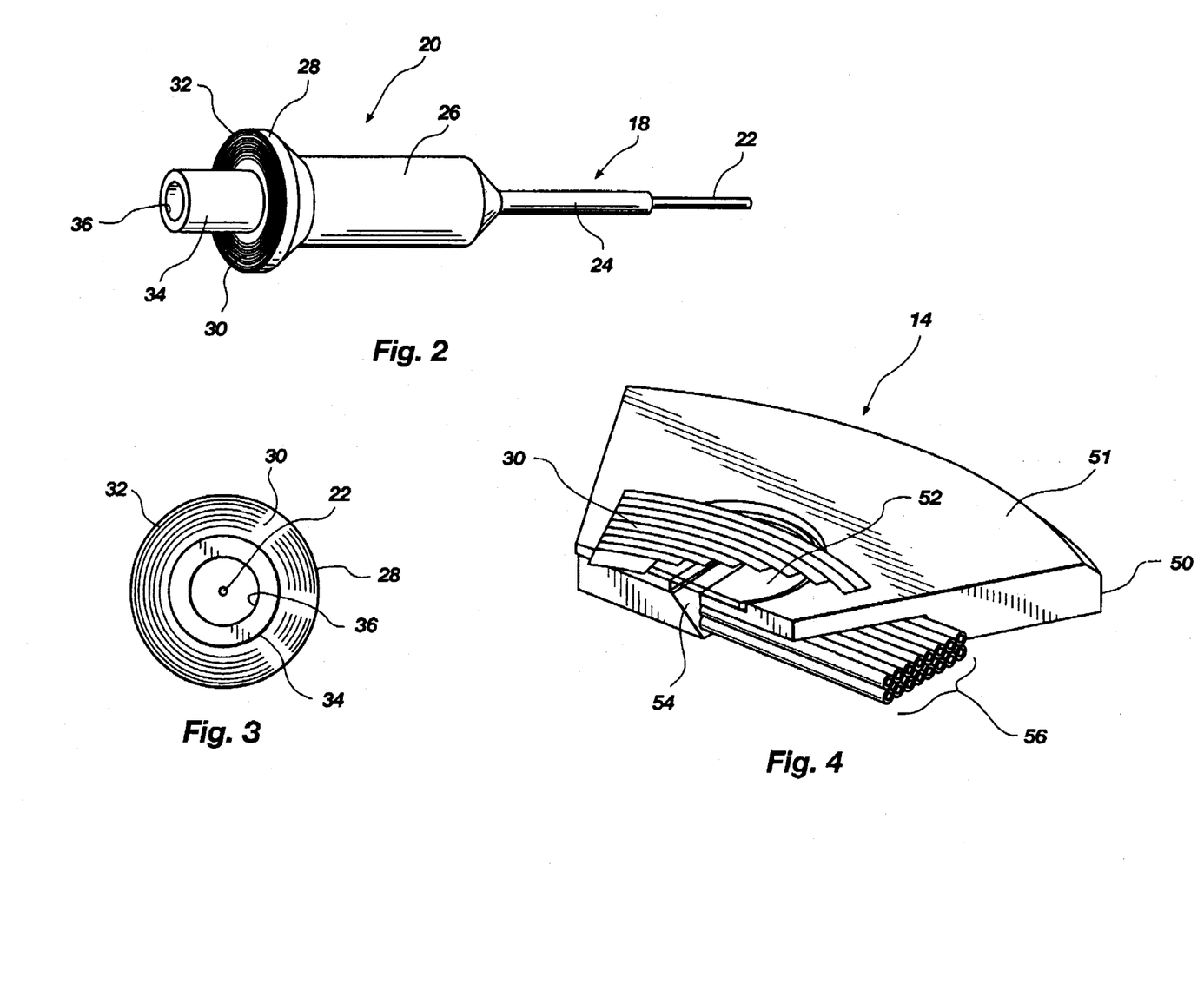
FIG. 2 is a perspective view of an exemplary fiber-optic plug in accordance with the present invention.
FIG. 3 is an elevated end view of the fiber-optic plug illustrated in FIG. 2.
FIG. 4 is a sectional view of a first preferred fiber-optic receptacle in accordance with the present invention.

FIG. 2 provides a perspective view of a preferred fiber-optic connector plug 20 in accordance with the present invention. The illustrated fiber-optic connector plug 20 is connected to an optical fiber assembly 18 which includes an optical fiber 22 and a protective sheath 24. The optical fiber assembly 18 is held at one end by a plug body 26. The plug body is preferably configured to allow a user to conveniently grasp the same and which can be fabricated from materials known in the art.

Extending from one end of the plug body 26 is a cylinder 34 having a cylindrical tunnel 36 provided therein. The cylinder 34 mates with corresponding structures in the receptacle (14 in FIG. 1) to ensure precise alignment of the optical components as known in the art. The plug body 26 is also provided with a collar 28 around the cylinder 34. The collar 28 ensures that the cylinder 34 will be inserted into the receptacle 14 (FIG. 1) to the appropriate distance and provides other functions as will be explained shortly.

FIG. 3 is an elevated end view of the fiber-optic connector plug represented in FIG. 2. FIG. 3 clearly shows the collar 28, the cylinder 34, and the end of optical fiber 22 which is enclosed within the protective sheath (24 in FIG. 2). The end of the optical fiber 22 is highly polished and the represented structures provide precise alignment of the end of the optical fiber 22 with a corresponding optical component which outputs the laser light and which is terminated at the receptacle (14 in FIG. 1).

Still referring to FIG. 3, provided on the face 30 of the collar 28 is a coded symbol 32 which, in the illustrated embodiment, is a pattern of concentric annular rings of either reflective or absorptive optical characteristics disposed about the cylinder 34. Each of the concentric annular rings is an example of an information zone.

The coded symbol 32 can be one of any number of optically read symbols which are capable of conveying information from the face 30 to an appropriate detection device, as will be explained shortly. Numerous coded symbols can be selected from those available in the art, such as coded symbols commonly referred to as bar codes. Information regarding such alternative coded symbols which can be incorporated into the embodiments of the present invention is available from the publication entitled Palmer, Roger C., *The Bar Code Book* (1989 Helmers Publishing, Inc.) which is now incorporated herein by reference in its entirety. While other symbologies can be used, the illustrated coded symbol 32 comprising a plurality of concentric and continuous circles or a variation thereof, is particularly advantageous when used with the present invention as will be explained shortly. It will be appreciated that the representation of the coded symbol is merely diagrammatic and that appearance of the coded symbol 32 will vary in accordance with the particular symbology selected. While it is preferred to utilize an optically read coded symbol, it is also within the scope of the present invention to utilize a machine readable symbol which is not necessarily also optically readable by a machine.

Once a particular appliance which is known to the laser device (10 in FIG. 1) is mated with the receptacle (14 in FIG. 1), the coded symbol conveys information for the appliance so that the laser device 10 can be calibrated and/or operated accordingly. If the appliance 12 is not recognized by the laser device 10, then it is preferred that the laser device 10 prevents operation until corrective action is taken to avoid operation in an incorrect or unsafe manner. Further information regarding examples of the structures used to detect the coded symbol 32 will be discussed shortly.

It will be appreciated that the coded symbol which is used to carry out the present invention need not be arranged as concentric annular rings as represented in FIG. 3. One arrangement would be to include only an arcuate pie-shaped section of the concentric annular rings. Moreover, another alternative arrangement would be to provide discrete sets of arcuate segments of concentric annular rings where each discrete set of concentric annular rings convey information in addition to, or redundant of, the information conveyed by the other sets of concentric annular rings. The particular advantage of the concentric circular information zones of the coded symbol represented in FIG. 3 is that the information contained therein is accurately conveyed regardless of the rotational orientation of the plug 20 in the laser device receptacle (14 in FIG. 1).

It will further be appreciated that symbologies commonly referred to as bar codes, as suggested above, can also be used. Many such bar code symbologies which are in use concentrate on densely packing digital information into a small location thus increasing the complexity of the necessary detection structures. In contrast, the illustrated coded symbol 32, and the accompanying detection structures described herein, are robust, reliable, and economically implemented.

Most advantageously, the coded symbol 32 allows the same plug 20 (as seen best in FIG. 2) to be used with laser devices with physically compatible receptacles (see 14 in FIG. 1) but which are not provided with the structures necessary for detection of the coded symbol. Moreover, the illustrated plug 20 structure is simple and reliable. There advances are particularly important in view of the complicated structures which have been previously available and which can only be used with laser devices provided with similarly complicated receptacle structures. The preferred detection structures for use with the illustrated plug 20 will be described next.

Reference will next be made to FIG. 4 which is a sectional view of a first preferred fiber-optic receptacle represented at 14 in FIG. 1. Illustrated in FIG. 4 is a receptacle plate 50 which is provided with a planar front surface 51. The receptacle plate 50 is mounted on the housing of the laser device (10 in FIG. 1) and functions as a principle component of the receptacle (14 in FIG. 1).

Figure 5:
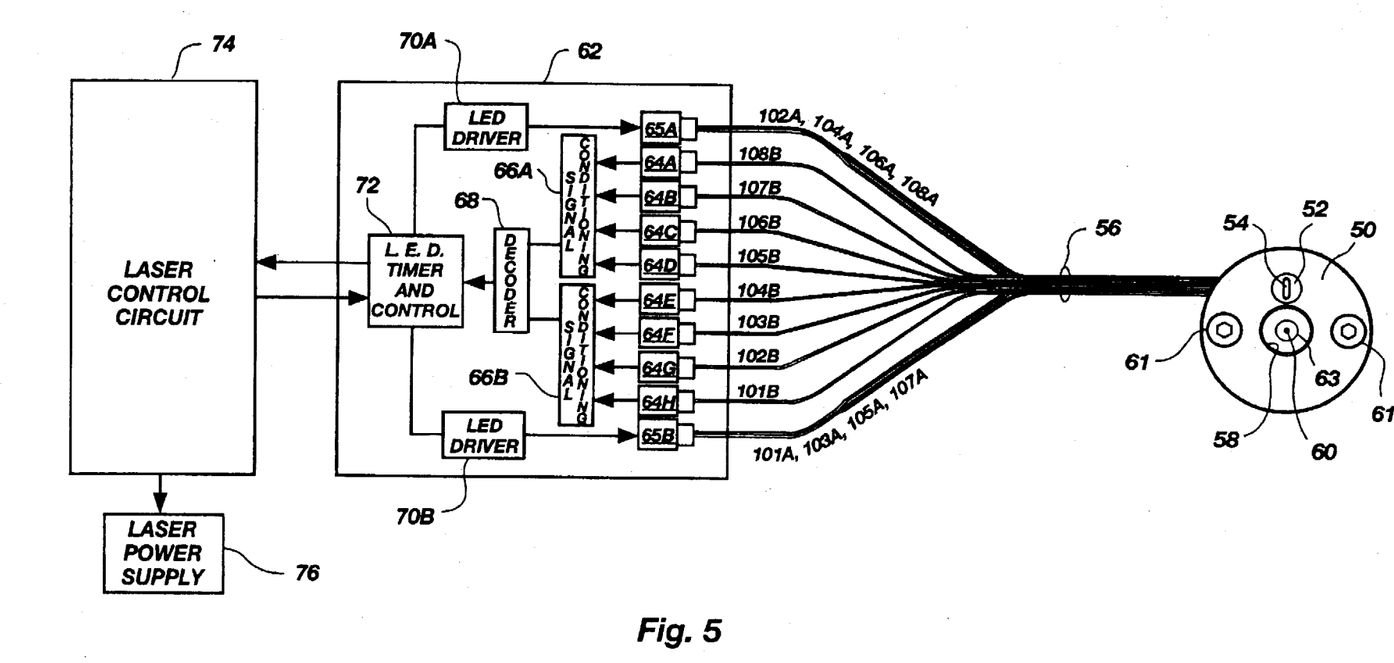
FIG. 5 is a diagrammatic view of the first fiber-optic receptacle illustrated in FIG. 4 and a block diagram of showing a first preferred arrangement of the interface and control circuits of the present invention.

The planar front surface 51 allows the face 30 of the collar 28 to rest thereon. It will be understood that the aperture which is provided in the receptacle plate 50 to receive the cylinder 34 of the plug 20 is not represented in FIG. 4 but is represented in FIG. 5.

A port is provided in the planar front surface 51 which is covered by a window 52. The concentric annular rings 30 of the coded symbol 32 are represented in FIG. 4 in the position they assume, flat against the window 52, when the face 30 of the collar 28 (not represented in FIG. 4) is fully facing the planar front surface 51. A mirror 54 reflects the image of each of the concentric annular rings of the coded symbol 32 into a respective optical fiber of a set of optical fibers indicated at bracket 56.

As can be seen in FIG. 4, one coded symbol 32 preferred for use with the present invention comprises eight annular rings, or information zones, which can each be either reflective or absorptive at whatever wavelength of light which is being used to detect the information embedded in the coded symbol 32. With eight annular regions, representing eight digital bits, a total of 256 parameters can be communicated regarding the appliance (12 in FIG. 1). The parameters can be any of those mentioned earlier (e.g., maximum continuous wave power handling capacity, a range of wavelengths at which operation is most efficient, a laser pulse width which is most effective, limitations as to duty cycle, the total energy which can be delivered per pulse train, and so forth). It is also within the scope of the present invention that the coded symbol be used to identify a particular appliance 12, rather than the individual parameters of the appliance 12. Thus, once a particular appliance which is known to the laser device (10 in FIG. 1) is mated with the receptacle (14 in FIG. 1), the particular parameters for the appliance can be looked up and the laser device 10 operated accordingly. If the appliance 12 is not recognized by the laser device 10, then it is preferred that the laser device 10 cease operation until corrective action is taken to avoid operation in an incorrect or unsafe manner.

The arrangement of the set of optical fibers 56 represented in FIGS. 4 and 5 will now be explained. FIG. 5 provides a diagrammatic representation of the receptacle plate 50 and the structures associates therewith as well as an interface circuit 62, a laser control circuit 74, and a laser power supply 76. FIG. 5 shows that the receptacle plate 50 is provided with an aperture 58. Also provided is an assembly 63 having an optical fiber 60 at the center thereof from which the output of the laser is emitted. It will be understood that the corresponding structures of the plug (20 in FIG. 2) mate with the receptacle structures represented in FIG. 5. Bolts 61 are used to hold the receptacle plate 50 in place.

The mirror 54 can be seen though the window 52 in the view of FIG. 5. The set of optical fibers 56 are represented emerging from under the receptacle plate 50 where they are held in place adjacent to the mirror 54 by structures which can readily be devised by those skilled in the art. Each of the fibers in the set of optical fibers 56 carries out a particular function as will now be explained referring to FIGS. 5–7.

In the first preferred arrangement represented in FIG. 5, fibers 102A, 104A, 106A, and 108A are optically coupled to an LED 65A which is powered by an LED driver 70A while fibers 101A, 103A, 105A, and 107A are optically coupled to an LED 65B which is powered by an LED driver 70A. The remaining fibers are individually optically connected to respective photo detectors 64A–64H, i.e., fiber 101B is coupled to photodetector 64H, fiber 102B is coupled to photodetector 64G, fiber 103B is coupled to photodetector 64F, fiber 104B is coupled to photodetector 64E, fiber 105B is coupled to photodetector 64D, fiber 106B is coupled to photodetector 64C, and fiber 107B is coupled to photodetector 64B, fiber 108B is coupled to photodetector 64A.

Figure 6:
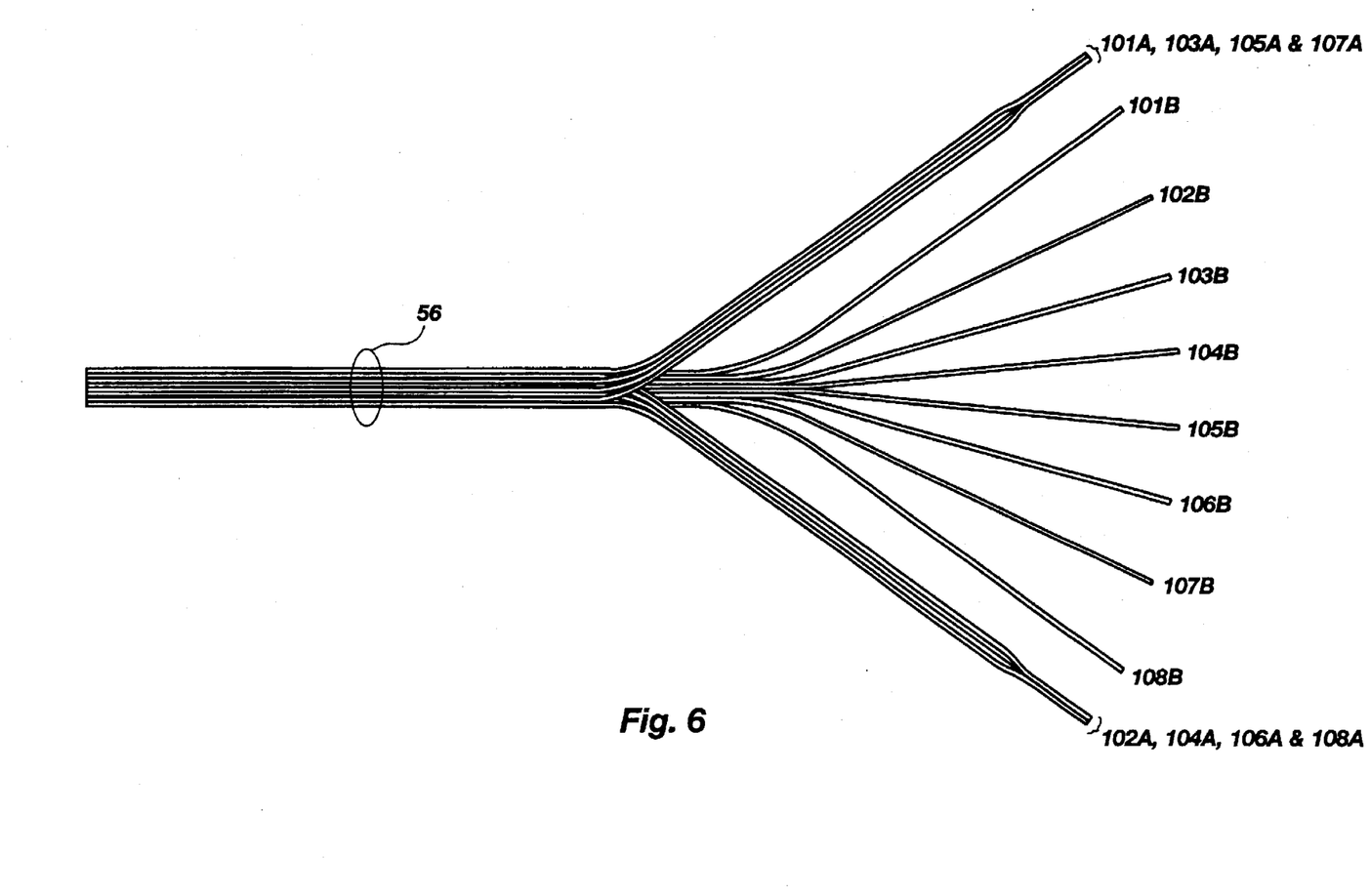
FIG. 6 is a detailed plan view representation of the arrangement of the sensing fibers represented in FIGS. 4 and 5.
Figure 7:
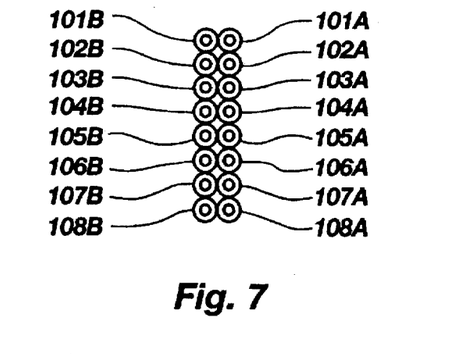
FIG. 7 is a cross sectional detailed representation of the arrangement of the sensing fibers represented in FIGS. 4–6.

FIG. 6 shows fibers 101A, 103A, 105A, and 107A are joined together as they are connected to LED 65A (FIG. 5). Likewise, FIG. 6 also shows fibers 102A, 104A, 106A, and 108A are joined together as they are connected to LED 65B (FIG. 5). FIG. 7 shows the arrangement of the fibers of the set of optical fibers 56 as they terminate adjacent to the mirror 54. As can be seen in FIG. 7, the fibers which are connected to the LEDs 65A & 65B are positioned directly adjacent to their corresponding fibers which are connected to their respective photodetector 64A–64H. As represented best in FIG. 4, the arrangement shown in FIG. 7 provides that the fiber 101A–108A connected to one of the LEDs 65A or 65B is aligned with one respective concentric annular ring of the coded symbol 32 and aligned with the appropriate fiber 101B–108B connected to one of the photodetectors 64A–64H.

Referring now again to FIG. 5, one preferred structure used to detect the reflectance or absorption of a particular concentric annular ring of the coded symbol 32 will be explained. For purposes of this explanation, the operation of fibers 101A and 101B will be representative of the operation of all of the fibers of the set of fibers 56. The light from the LED 65B is transmitted into fiber 101A which is one of four fibers (101A, 103A, 105A, and 107A) connected to LED 65B. As best explained by reference to FIG. 4, the light is transmitted by the fiber 101A and is emitted from the end of the fiber 101A into the mirror 54. The light emitted from the end of the fiber 101A is reflected by the mirror 54, passes through the window 52, and illuminates the concentric annular ring which is located directly in line with the two fibers 101A and 101B. The light which is reflected from the concentric annular ring which has been illuminated passes back through the window 52, is reflected from the mirror 54, and enters the fiber 101B. The light which exits the end of fiber 101B is transmitted into a photo-detector 64A. If the corresponding concentric annular ring of the coded symbol 32 is reflective, the output of the photodetector, 64A in FIG. 5, will represent a logical 1. If the concentric annular ring of the coded symbol 32 is non-reflective, e.g., a flat black, very little light will be returned to the photo detector and the output of the photodetector, 64A in FIG. 5, will represent a logical 0. It will be appreciated that those skilled in the art can arrive at many different arrangements which can be used to detect the information embedded in the coded symbol 32 using the information contained herein.

In order to improve the reliability of the arrangement represented in FIG. 5, the LEDs 65A & 65B are operated at a 25% (or less) on time duty cycle and are shifted in phase from one another by 180 degrees by the components of the interface circuit 62 using techniques known in the art. It will be appreciated that by illuminating the coded symbol so that the concentric annular rings which correspond to even-numbered fibers (102, 104, 106, and 108) of the set of fibers 56 are alternatively illuminated in turn with those which correspond to odd-numbered fibers (101, 103, 105, and 107) and by gating the photo detectors 64A–64H on and off in a similar fashion, adjacent channel interference can be eliminated. While the exemplary operation of the illustrated arrangement using fibers 101A and 101B has been described, the preferred operation is the same for all fiber-optic pairs.

Still referring to FIG. 5, with both LEDs 65A & 65B and the photodetectors 64A–64H being operated in the described fashion, the output of each of the photodetectors 64A–64H is conveyed to signal conditioners 66A & 66B. The output of the signal conditioners 66A & 66B is passed along to a decoder 68 whose output is input to an LED timer and control circuit 72. The LED timer and control circuit communicates with a laser control circuit 74 which generally controls the operation of the laser device 10 (FIG. 1) which in turn controls the operation of the laser power supply 76 or other components as will be appreciated by those skilled in the art.

Figure 8:
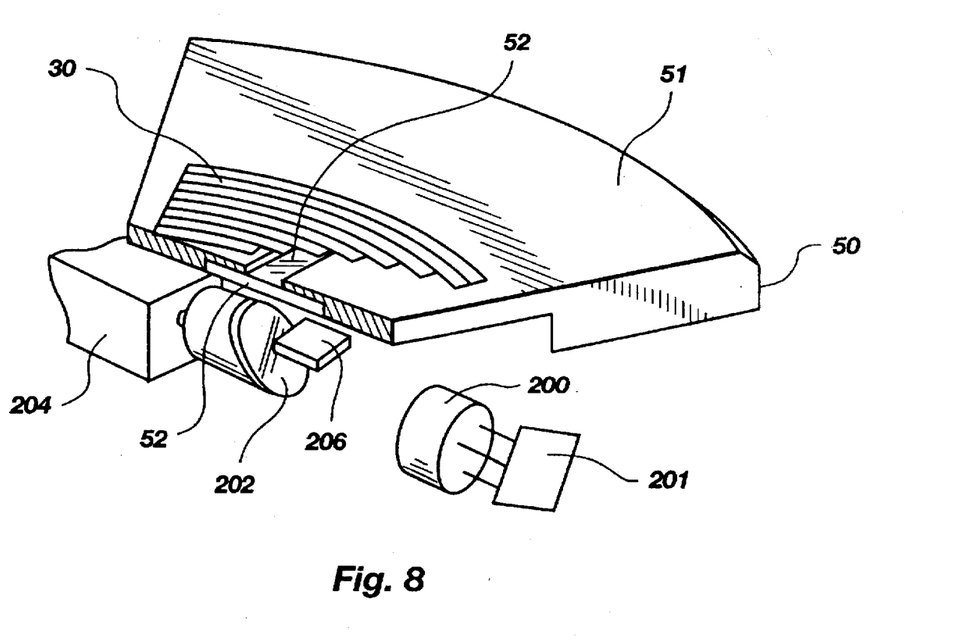
FIG. 8 is a sectional view of a second preferred fiber-optic receptacle in accordance with the present invention.
Figure 9:
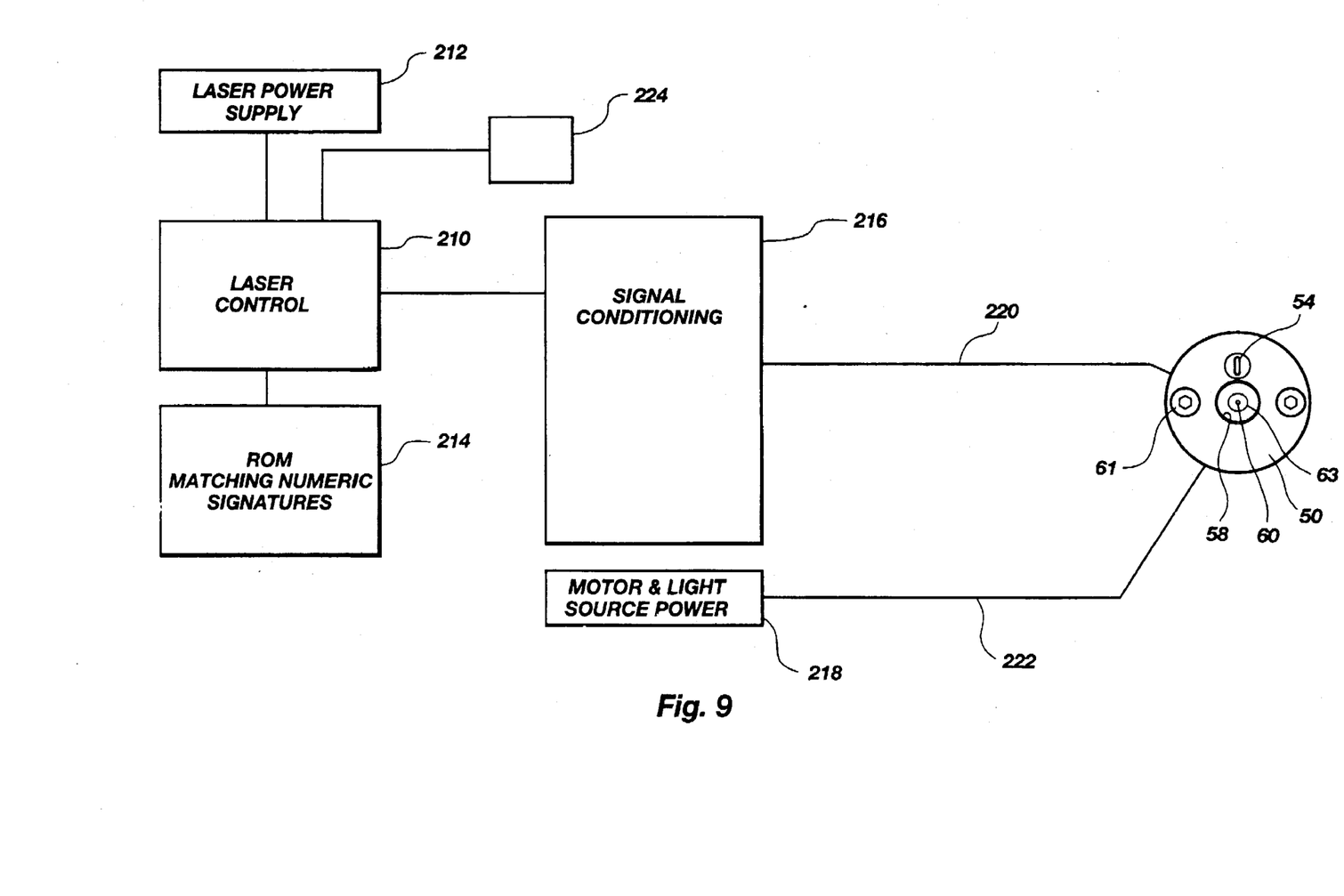
FIG. 9 is a diagrammatic view of the second fiber-optic receptacle illustrated in FIG. 8 and a block diagram of showing a second preferred arrangement of the interface and control circuits of the present invention.

While the arrangement represented in FIGS. 4–7 is simple and reliable, the amount of information about the appliance, or about the operation of the laser device/appliance combination, which can be conveyed to the laser device may be less than desired. In many cases, as will be explained, it will greatly enhance the safety and convenience of the operation of the laser device if more information about the appliance is conveyed to the laser device. FIGS. 8 and 9 will be used to describe a second preferred arrangement which allow the plug (FIGS. 2 and 3) to convey additional information to the laser device.

Reference will next be made to FIG. 8 which is a sectional view of a second preferred fiber-optic receptacle such as that represented at 14 in FIG. 1. Those skilled in the art will readily appreciate which of the arrangements described herein are preferred for incorporation into a laser device in accordance with the particular end use of the laser device. Illustrated in FIG. 8 is the receptacle plate 50 which is provided with a planar front surface 51. The receptacle plate 50 is mounted on the housing of the laser device (10 in FIG. 1) as described earlier. The planar front surface 51 allows the face 30 of the collar 28 (FIG. 2) to rest thereon. A port is provided in the planar front surface 51 which is covered by a window 52. The concentric annular rings 30 of the coded symbol 32 are represented in FIG. 8 as explained earlier.

As seen in FIG. 8, various detection components are provided below the receptacle plate 50. A light source 200, which preferably comprises an LED, is provided. Along with the light source 200, appropriate focusing optics are provided, including a focusing actuator 201, to ensure that a correctly formed spot (as known in the art) is reflected off a mirror 202 and onto the concentric annular rings 30.

The mirror 202 is oriented so that when it rotates by the action of motor 204 the spot generated by the light source 200 scans across the concentric annular rings 30. The light which is reflected from off the concentric annular rings 30 is received by a photodetector 206 as known in the art. Using the arrangement represented in FIG. 8, which utilizes a scanning beam to read the concentric annular rings 30, allows a considerable amount of information to be embedded into whatever symbology is used.

Reference will now be made to FIG. 9 which provides a diagrammatic representation of the receptacle plate 50 and the structures associated therewith as well as a signal conditioning circuit 216, a laser control circuit 210, a laser power supply 212, and a motor and light source power circuit 218. The motor and light source power circuit 218 conveys instructions to the motor 204 and the light source 200 via line 222. The signal conditioning circuit 216 receives a signal from the photodetector 206 (FIG. 8) via line 220. The signal conditioning circuit 216 carries out functions such as those explained earlier in connection with the interface circuit 62 and those functions which can be arrived at by those knowledgeable in the industry using the information set forth herein.

Also represented in FIG. 9 is a non-volatile memory 214 which is adapted to store information needed by the laser control circuit 210 in determining operating parameters and whether or not to fire the laser. A display 224, which may be any of the visual displays which are now known in the industry or which may become available in the future, is also preferably included in the system represented in FIG. 9.

As appreciated by those experienced in the industry, the role of medical lasers has greatly increased in recent years. The number of different treatments which can be successfully carried out on a patient has greatly increased due to the availability of laser devices to output laser light of different characteristics. Some medical laser devices allow characteristics such as power, color, and duration to be varied according to the treatment to be given to each patient.

As the adaptability of medical laser devices has increased, so has the potential for incorrect usage and the patient harm which results therefrom. Since medical practitioners are often concentrating on matters such as the condition and comfort of the patient while preparing for a treatment session, the present invention's automatic recognition of the parameters of the appliance and the automatic operation of the laser device in accordance with the laser parameters is a great advance providing ease of operation and safety not previously available.

Using an appropriate symbology, significant amounts of useful appliance parameters can be embedded into the coded symbol. When selecting a symbology, factors such as the following should be considered: the number of bits; the number of characters; the inclusion of start and stop bars; whether the symbology self-checking; whether the code continuous; whether the elements of the symbology of a fixed width; whether the code self clocking; and whether unidirectional or bi-directional reading of the symbology will be used.

It is preferred that the appliance convey one or more codes to the laser control circuit which, when recognized by the processor included in the laser control circuit 210, will represent appliance or treatment parameters and the operation of the laser device will automatically conform thereto. To this end, the non-volatile memory 214 can provide a look-up table for the codes and instructions for the laser control circuit 210 which accompany the receipt of a particular code. Those skilled in the art, using the information set forth herein, will be able to readily arrive at the programming code which is necessary to operate the embodiments of the present invention.

Discussed below are examples of information which can preferably be conveyed from the appliance to the laser device in accordance with the present invention. It will be understood that an appliance and laser device may only require that one of type of the information discussed herein be conveyed or that all of the information discussed herein be conveyed to the laser device in accordance with the treatment(s) to be carried out.

A. Personnel protection parameters are preferably communicated from the appliance to the laser device. Such parameters involve characteristics which are important to the safety and protection of both the patient and the medical practitioner. A shutter requirement parameter indicates whether a shutter must be used and a shutter type parameter indicates what type of shutter should be used and a shutter color parameter also indicates what color of shutter should be used. A protective eyewear parameter preferably causes a warning message to be provided telling the medical practitioner to use eyewear protection.

B. Laser device treatment color parameters are preferably communicated in the case of a laser device which provides multi-color operation. The appliance preferably communicates a laser treatment color options parameter to indicate which colors the appliance can be used with.

C. Treatment application parameters are preferably communicated from the appliance to the laser device. The treatment application parameters preferably include one or more of the following: a set power of the laser parameter; a set duration and dwell of the laser parameter; a set laser aiming base intensity parameter; and, an appliance illumination intensity parameter.

D. Appliance and laser device operation settings parameters are preferably communicated from the appliance to the laser device. For example, a treatment spot size parameter can be communicated in appropriate instances. Also, an aspiration volume parameter and an irrigation volume parameter are beneficially communicated where aspiration and irrigation functions are provided and desirable. A camera parameter can preferably be included to indicate the operation of a video or other camera. A cooling options parameter can also be preferably included when a cooling function is provided.

E. Appliance and laser device maintenance message parameters are preferably included and cause messages to be placed on a visual display or conveyed via an aural device. Among such parameters which can preferably be communicated are: a laser calibration message parameter; an appliance calibration message parameter; a power meter message parameter; a camera message parameter; and, a laser device and appliance cleaning and maintenance message parameter.

F. Treatment information parameters are preferably included and cause messages to be provided to the user. Such parameters preferably include a typical treatment descriptions message parameter, a typical laser device and appliance settings message parameter, and a typical procedural overview message parameter.

G. Appliance and laser device usage parameters, such as an appliance usage parameter, a cumulative laser energy used parameter, and a laser power used parameter, are also preferably communicated.

It will be appreciated that the apparatus of the present invention is easily operated by medical practitioners. In a preferred example, the medical practitioner inserts the plug (FIGS. 2 and 3) into the receptacle (FIGS. 5 and 9). The system automatically reads from the plug a first appliance parameter for the removable appliance and carries out a first parameter action in accordance with the first appliance parameter. The system also automatically reads from the plug a second, or more, appliance parameter for the removable appliance and the corresponding second parameter actions are carried out. The system is then used for treating a patient.

One advantageous feature of the present invention provides that each appliance is provided with a unique code. Each time an appliance is used to treat a patient, the unique code is read and/or compared to the codes of other appliances used to treat patients. If the current appliance code matches a prior code, and the appliance is one which is designed for only a single use, the laser device is prevented from operating unsafely with that appliance. Alternatively, if the appliance has been designed for use no more than a predetermined number of times, and the number of times has been exceeded, the laser device is prevented from operating unsafely with that appliance.

In view of the foregoing, it will be appreciated that the present invention provides a connector which simply and reliably conveys information between a plug and a receptacle of a connector and which is particularly adapted for use with medical lasers. The present invention also provides a fiber-optic plug and receptacle which provides automatic recognition of an appliance and which is inexpensive, so inexpensive that the plug does not prevent the entire appliance and plug being disposed of after a single use. The present invention also improves the safety of medical lasers by preventing improper calibration of a medical laser but allowing the connector to still be compatible with receptacles which are not equipped to detect the information conveyed by the plug.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for communicating information from a detachable appliance to a base unit so that the base unit can operate in accordance with the characteristics of the detachable appliance, the system comprising:

plug means for receiving energy which is output from the base unit, the plug means having an external surface which can be held by a user, and an optical fiber connection means for conveying laser light from the receptacle means and means for aligning the optical fiber connection means with the receptacle means;

means, connected to the plug means, for conveying energy received from the base unit to a location away from the base unit the means for conveying energy comprising an optical fiber and a hand piece;

receptacle means, mounted on the base unit, for operatively receiving the plug means and transferring energy from the base unit to the detachable appliance;

information bearing means, mounted on the plug means and oriented substantially perpendicularly to the external surface, the information bearing means being a substantially planar surface oriented perpendicularly to the external surface and adapted for presenting machine readable and optically readable information thereon;

coded symbol means for conveying information concerning the detachable appliance, the coded symbol means comprising a plurality of information zones, each information zone selectively consisting of a substantially optically reflective material or a substantially optically nonreflective material, wherein the information zones are arranged in concentric annular rings so that each information zone is passed over by a line extending tangentially from the external surface of the plug means;

means for detecting, connected to the receptacle means, the presence of a reflecting or nonreflecting material in each of the information zones, the means for detecting comprising:
  a light source generating a light beam;
  means for scanning the light beam across at least some of the information zones; and
  means for detecting variations in intensity of the light beam as it scans across the information zones; and means for decoding, connected to the means for detecting and comprising a processor means, the information conveyed by the coded symbol means such that one or more characteristics of the detachable appliance can be automatically identified to the base unit.

2. A system for communicating information from a detachable appliance to a base unit as defined in claim 1 wherein the coded symbol means comprises eight information zones.

3. A system for communicating information from a detachable appliance to a base unit as defined in claim 1 wherein the means for decoding further comprising signal conditioning means.

4. A system for communicating information from a detachable appliance to a base unit as defined in claim 1 wherein the system comprises a medical appliance attached to said optical fiber.

* * * * *